United States Patent [19]
Senevat et al.

[11] Patent Number: 5,577,088
[45] Date of Patent: Nov. 19, 1996

[54] METHOD AND DEVICE FOR ULTRASONIC EXAMINATION OF FACES OF THE INTERNAL SURFACE OF THE WALL OF CLADDING

[75] Inventors: Jean Senevat, Saint Brevin les Pins; Christian Roy, Grand Champ des Fontaines; Eric Lucas, Nantes, all of France

[73] Assignee: Zircotube, Courbevoie, France

[21] Appl. No.: 393,739

[22] Filed: Feb. 24, 1995

[30] Foreign Application Priority Data

Feb. 25, 1994 [FR] France .................................. 94 02214

[51] Int. Cl.⁶ .................................................. G21C 17/00
[52] U.S. Cl. ........................ 376/252; 376/258; 376/247; 376/457
[58] Field of Search ..................... 376/252, 258, 376/247, 457; 73/622, 624, 625, 637, 638, 648, 649

[56] References Cited

U.S. PATENT DOCUMENTS

| | | | |
|---|---|---|---|
| 3,961,523 | 6/1976 | Cornforth | 73/67.83 |
| 4,126,514 | 11/1978 | Wonn | 376/252 |
| 4,441,369 | 4/1984 | Lessard et al. | 73/602 |
| 4,843,884 | 7/1989 | House et al. | 73/622 |
| 4,918,989 | 4/1990 | Desruelles et al. | 73/627 |
| 5,063,780 | 11/1991 | Landry et al. | 73/622 |
| 5,454,267 | 10/1995 | Moreau et al. | 73/623 |

FOREIGN PATENT DOCUMENTS

| | | |
|---|---|---|
| 2363356 | 6/1975 | Germany . |
| 2557062 | 6/1977 | Germany . |

OTHER PUBLICATIONS

Search Report FR 94 02214.
PCT/DE90/00204.
Abstracts of Japan, vol. 8, No. 97 (P-272) "Method for Discriminating Wall Thickness of Pipe Body".

*Primary Examiner*—Charles T. Jordan
*Assistant Examiner*—Meena Chelliah
*Attorney, Agent, or Firm*—Pollock, Vande Sande & Priddy

[57] ABSTRACT

The tubular cladding (1) comprises an internal surface of substantially prismatic shape, having successive faces. An ultrasonic examination head (3) makes it possible to emit ultrasound waves in the form of pulses from the outside of the cladding (1), so that the ultrasound waves pass through the wall of the cladding (1) and scan the wall over its entire periphery. The frequency of the ultrasound pulses is adjusted as a function of the circumferential scanning speed of the cladding (1). An ultrasound signal reflected by the internal surface of the cladding (1) is recorded and the reflected signal is analyzed in order to examine the number and the amplitude of the faces and the variation in thickness of the tubular cladding (1) over one revolution.

11 Claims, 2 Drawing Sheets

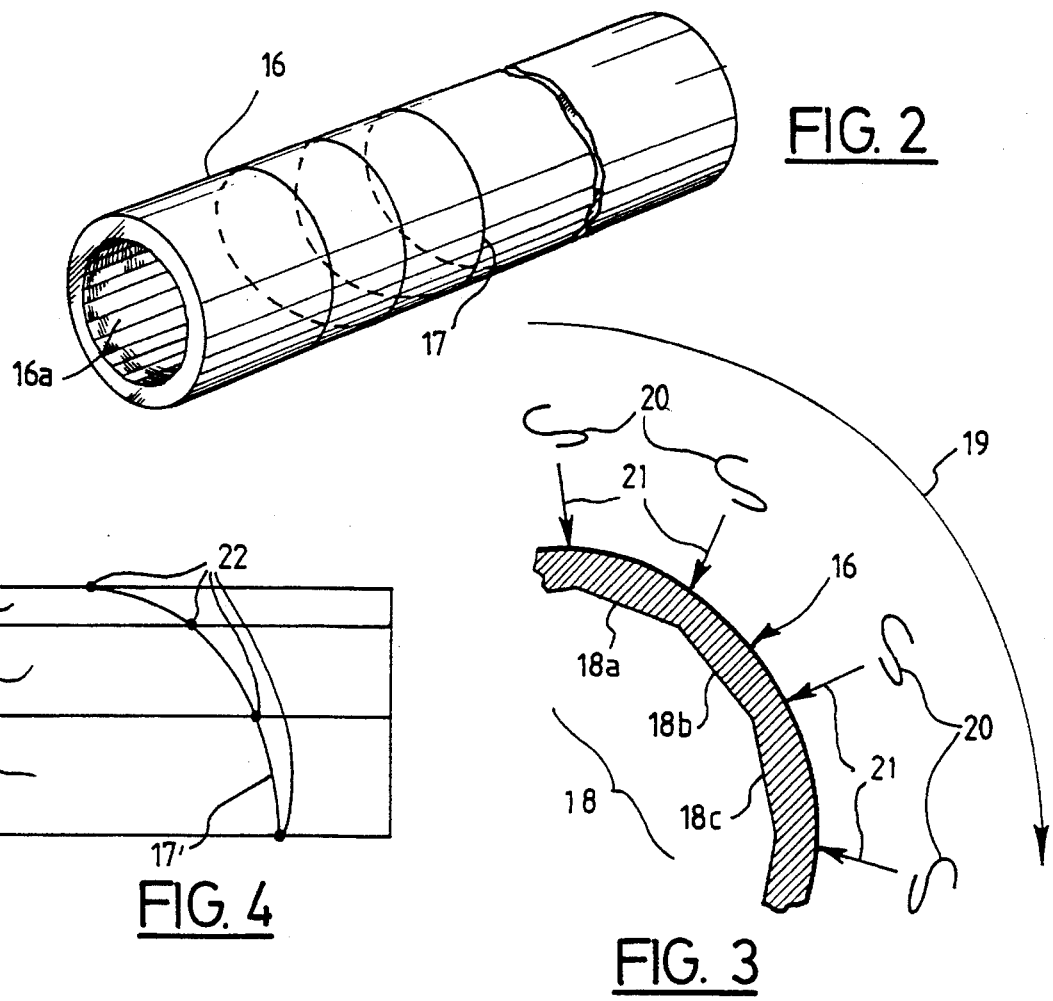
FIG. 2
FIG. 3
FIG. 4
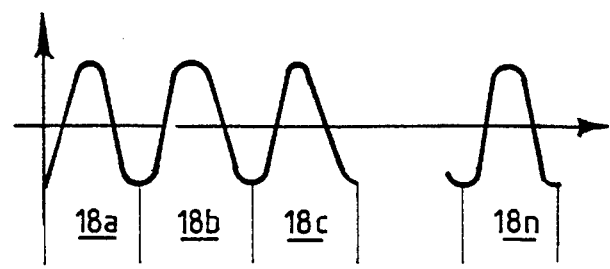
FIG. 5

5,577,088

METHOD AND DEVICE FOR ULTRASONIC EXAMINATION OF FACES OF THE INTERNAL SURFACE OF THE WALL OF CLADDING

FIELD OF THE INVENTION

The invention relates to a method and a device for ultrasonic examination of faces on the internal surface of the wall of tubular cladding, in particular the cladding of a fuel rod for a nuclear reactor.

BACKGROUND OF THE INVENTION

The fuel rods for a nuclear reactor generally comprise cladding of tubular shape and, inside the cladding, pellets of fuel material, generally made by sintering, which are stacked along the longitudinal direction of the tubular cladding.

Owing to the swelling of the fuel material pellets under irradiation, the peripheral part of the pellets comes into contact abutment, with a certain pressure, against the internal surface of the cladding, when the fuel is used in the core of a nuclear reactor.

This may result in interactions between the pellets and the cladding which may lead to damage of the cladding, promoted by the working temperature of the fuel.

It has been proposed to limit the possibilities of contact between the pellets and the cladding, in order to avoid as far as possible the drawbacks linked with this phenomenon which is called pellet-cladding interaction (PCI).

It has been proposed, for example, in the case of fuel for a reactor cooled by boiling water, to use cladding tubes whose internal surface comprises longitudinal grooves, so as to limit the area of contact between the pellets and the cladding, while allowing sufficient thermal transfer of the heat produced by the nuclear fuel to the outside of the cladding.

In the case of rods for fuel assemblies intended for pressurized water nuclear reactors, it has also been proposed to use tubular cladding whose prismatically-shaped internal surface consists of faces, all having the same width, which are arranged successively and regularly over the internal surface of the cladding.

With such a configuration, the fuel pellets which have a circular contour, are capable of coming into contact with the faces of the internal surface of the cladding, in zones which are isolated from one another, along the generatrices of the pellets.

According to this principle, cladding is produced which comprises thirty or forty faces over its internal surface.

In the context of development studies and manufacture of tubular cladding comprising faces over its internal surface, it is necessary to provide a method for examining the faces on the internal surface of the tubular cladding.

In particular, it is necessary to examine the number of faces over the entire internal periphery of the tube and the width of the faces in the peripheral direction. An examination must indeed be made as to whether all the tubes leaving manufacture have the same number of internal faces and whether the faces have the same amplitude over the periphery of the internal surface of the cladding and over the entire length of the tube.

In order to examine the thickness of the fuel rod cladding at the end of manufacture, it is known to use an ultrasonic examination head of annular shape which is engaged in a coaxial position around the tubular cladding to be examined and which is rotated about its axis at high speed.

The ultrasonic examination head comprises one or more transducers which emit ultrasound waves in substantially radial directions towards the inside of the tube. In order to carry out the thickness examination of the tube continuously or in successive zones along its length, a relative displacement of the tube and of the rotating examination head is produced so as to scan the entire peripheral surface of the tube along a helicoid trajectory by a beam of ultrasound waves.

Analysis of the signal corresponding to the ultrasound waves reflected from the internal surface of the tubular cladding makes it possible to carry out a thickness measurement and examination of the tubular cladding.

When use is made of ultrasound waves which are emitted in the form of successive pulses or wave trains, measurements can be made at isolated points distributed over the periphery of the tube, the number of measurement points on the periphery of the tube, i.e., over one complete revolution, depending on the speed of rotation of the examination head and on the repetition frequency of the ultrasound wave trains. However, such a measurement procedure has never been used for examining the number and the amplitude of the internal faces of a multi-faced cladding tube. Furthermore, if such a method were to be used for examining faces, it would prove unusable insofar as the speed of rotation of the examination head and the constancy of this speed over time cannot be guaranteed with sufficient precision. For this reason, it is not possible to make accurately localized measurements with respect to the faces of the internal surface of the tubular cladding.

SUMMARY OF THE INVENTION

It is an object of the invention to provide a method for ultrasonic examination of faces on the internal surface of the wall of tubular cladding comprising an internal surface of substantially prismatic shape, having successive faces, this method making it possible, in particular, very precisely to examine the number of faces of the cladding and the amplitude of these faces in the peripheral direction of the internal surface of the cladding as well as the thickness variation of the cladding over one revolution.

According to this method ultrasound waves are emitted in the form of pulses from the outside of the cladding so that the ultrasound waves directed towards the inside of the cladding pass through the wall of the cladding_and scan the wall over its entire periphery, thee mission frequency of the ultrasound pulses is adjusted as a function of the circumferential scanning speed of the cladding, so that the emission frequency is equal to an integer multiple of the scanning frequency of the faces of the cladding, an ultrasound signal reflected by the internal surface of the wall of the cladding is recorded, and the reflected signal is analyzed in order to examine the faces.

The invention also relates to a device for carrying out the method for ultrasonic examination of the faces of tubular cladding.

BRIEF DESCRIPTION OF THE DRAWINGS

In order to explain the invention clearly, a description will now be given, by way of example, with reference to the attached drawings, of a device for carrying out the examination method according to the invention and its implementation for examining tubular cladding for fuel rods comprising faces on their internal surface.

FIG. 2 is a perspective view of tubular cladding for nuclear fuel, on which an examination is carried out using the method according to the invention.

FIG. 3 is a cross-sectional view of a part of a multi-faced tube on which an examination is carried out using the method according to the invention.

FIG. 4 is a view in projection on a diametral plane of the internal surface of the tube represented in FIG. 3.

FIG. 5 is a diagram showing a signal representing the thickness of a multi-faced tube during its examination using a method according to the invention.

DETAILED DESCRIPTION

Figure 1:
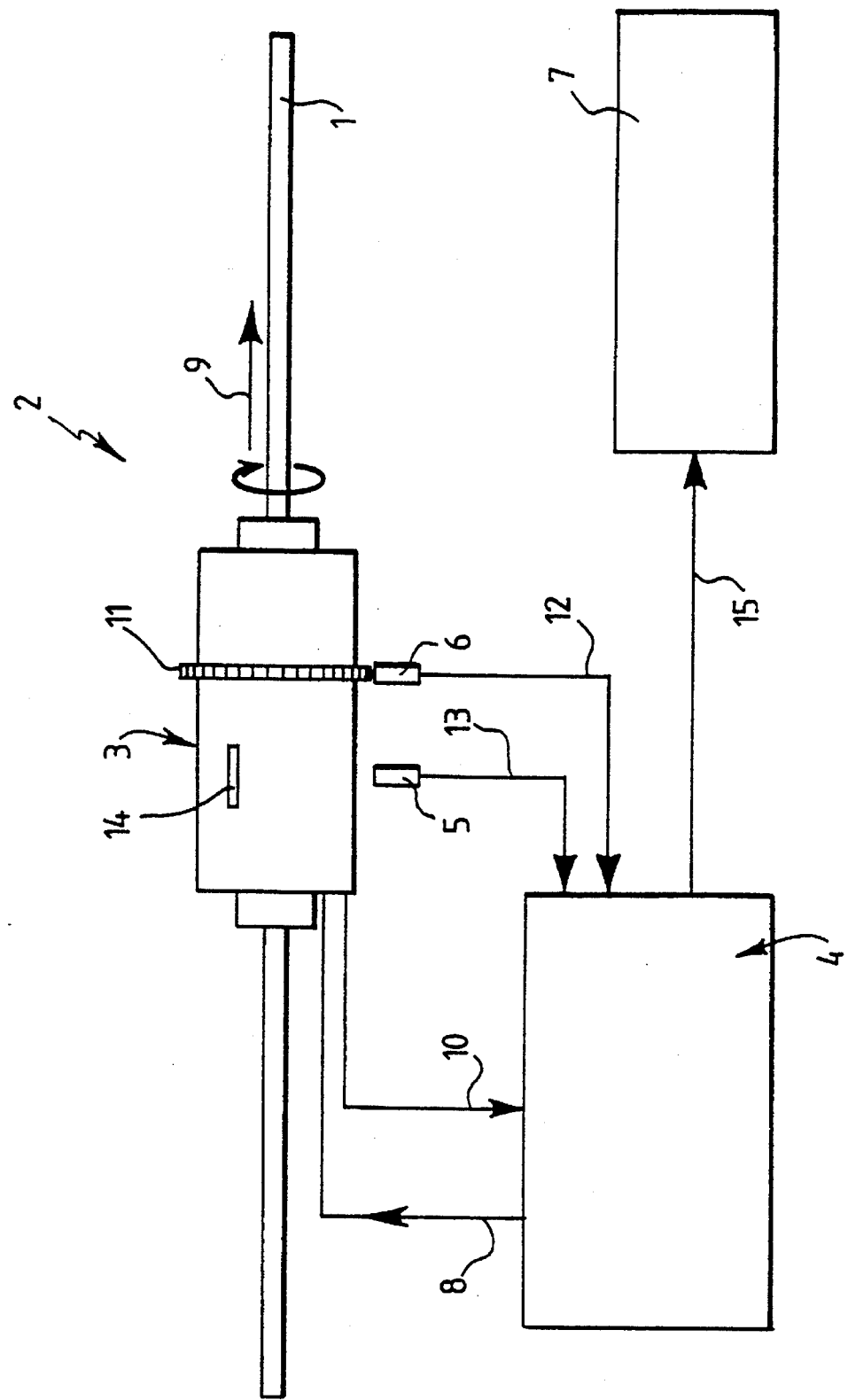
FIG. 1 is a schematic view of a device for carrying out the method according to the invention.

FIG. 1 shows a device for ultrasonic examination of tubular cladding 1 of a fuel rod 2 for a nuclear reactor.

The examination device 2 comprises an ultrasonic examination head 3 of tubular shape which is engaged, in a substantially coaxial arrangement, around the tube 1, a supply and processing unit 4, sensors 5 and 6 arranged in the vicinity of the outer lateral surface of the head 3 and an alarm device 7 connected to the output of the supply and processing unit 4.

The ultrasonic examination head 3 comprises a cylindrical body which can be driven in rotation at very high speed about its axis. The ultrasonic examination head 3 also comprises one or more transducers making it possible to emit ultrasound waves inwards towards the axis of the ultrasonic examination head and/or to pick up the ultrasound waves reflected by the tube 1 and, in particular, the ultrasound waves which have passed through the wall of the tube 1 and are reflected by the internal surface of the tube.

The transducers are supplied with electrical excitation current by a supply line 8 which connects the electric current supply circuit of the supply and processing unit 4 to the transducers of the examination head 3.

Ultrasonic examination of the thickness of the tubular cladding 1 of a fuel rod, over its entire length, can be carried out by moving the tube 1, within the examination head 3 and along its axis, as indicated by the arrow 9. The head 3 is rotated at very high speed so that helicoid scanning is produced, during movement of the tube in the direction of the arrow 9, of its entire wall by an ultrasound wave beam emitted by a transducer of the examination head 3.

It is also possible to move the head 3 both in rotation and in translation along the tube 1, in order to scan the wall of the tube 1.

An installation as represented in FIG. 1 can be used for carrying out thickness examination of tubular cladding having a smooth cylindrical internal surface.

The transducer of the examination head 3 is supplied with electric current so as to produce ultrasound waves in the form of wave trains or pulses at certain time intervals during the rotation and movement of the head with respect to the tube 1.

The ultrasound waves penetrate radially into the wall of the tube 1 and are reflected by its internal surface to be recovered by a transducer of the examination head 3.

The time shift between the emitted wave train and the reflected and recovered wave train gives the time of flight of the ultrasound through the wall of the tube and makes it possible to provide a signal representing the thickness of the tube, which is evaluated by the processing unit 4, on the basis of the reflected ultrasound wave signal which is sent to the processing unit 4 by the transmission line 10.

It is thus possible to obtain a signal which can be exploited for examining the thickness of the wall of the tube.

According to the repetition frequency of the ultrasound wave trains as a function of the speed of rotation of the examination head 3, it is possible to obtain a certain number of measurements per revolution of the examination head 3 about the tube 1, during rotation of the head 3 about the tube, making it possible to produce circumferential scanning of the tube i by the ultrasound waves.

In the case of a multi-faced tube 1, i.e., of a tube of which the internal surface of the wall has a prismatic shape consisting of successive plane faces having a substantially constant width in the circumferential direction, the thickness signal obtained by the device which has just been described does not in general make it possible to examine the number and the width of the faces of the tube 1.

Indeed, if the repetition frequency of the ultrasound pulses is independent of the scanning frequency of the faces of the tube by the ultrasound waves, the ultrasound waves are reflected by faces which are not generally successive faces of the tube and by-zones of these faces having an arbitrary position with respect to the edges of the prismatic surface.

No information can therefore be derived from the thickness-measurement signal as regards the faces of the tube 1.

According to the invention, the body of the examination head 3 carries a toothed ring 11 coaxial with the cylindrical casing of the examination head 3 and fixed on its external surface.

The sensor 6, which preferably consists of a Hall probe, is arranged facing the ring 11 so as to detect the passage of the teeth of the ring. The sensor 6 is connected by a conductor 12 to the processing unit 4.

The signal from the sensor 6 is used in the processing unit 4 for controlling the supply pulses of the transducer of the examination head 3, so that the repetition frequency of the ultrasound wave trains emitted by the transducer towards the wall of the tube 1 is equal to the scanning frequency of the faces of the tube 1 by the ultrasound waves, or to an integer multiple of this frequency.

Slaving the supply of the transducer to the signal from the sensor 6 makes it possible to produce this synchronization of the ultrasound pulses with respect to the scanning of the faces in a very simple manner and to avoid any drift resulting from variations in the speed of rotation of the examination head 3. Indeed, if the repetition frequency of the ultrasound wave trains is fixed at a certain value, corresponding to the scanning frequency of the faces, for a given speed of rotation of the examination head, a drift is very rapidly observed, because the speed of rotation of the examination head 3 cannot be fixed and kept at a sufficiently precise value to take the measurements in synchronism.

Such a measurement, carried out on the faces, would therefore not be stable and would undergo "desynchronization" after a few moments.

On the other hand, use of the synchronization sensor 6 makes it possible exactly to adjust the frequency of the ultrasound pulses to the speed of rotation of the head, regardless of this speed and its variations.

Use will be made of a toothed ring in which the number of teeth is an integer multiple of the number of faces of the tube 1.

For example, in the case of a tube 1 comprising a prismatic internal surface having thirty faces, use may be made of a ring comprising 120 teeth, so that passage of the teeth past the sensor 6 produces a signal whose frequency is four times higher than the scanning frequency of the faces of the tube 1. This signal makes it possible to control the supply of the transducer so as to produce ultrasound pulses whose frequency can be equal to the scanning frequency of the faces or to an integer multiple of this frequency, for example equal to four times the scanning frequency of the faces.

It is thus possible to take either a single thickness measurement for each of the faces, in a well-determined position of the face, for example along a joining edge, or else a plurality of measurements, making it possible to explore the face over its entire width.

The body of the examination head 3 furthermore carries, on its external surface, a reference indicator 14, for example made of magnetic material, the passage of which can be located by the sensor 5 which is connected by a conductor 13 to the processing unit 4.

The successive passages of the reference indicator 14 opposite the rotational examination sensor 5 make it possible to emit a signal representing the revolutions executed by the examination head 3 around the tube 1.

Comparison of the thickness signal and the signal representing the rotation of the head makes it possible to count the number of faces of the tube.

The processing unit 4 comprises a means for comparing the number of faces measured during one revolution of the examination head 3 with the desired number of faces, for example thirty.

In the event that a difference is detected, a signal is transmitted via the conductor 15 to the alarm unit 7, which emits a message for the attention of the operator in charge of the examination.

FIG. 2 shows multi-faced tubular cladding 16 comprising an internal surface 16a of prismatic shape and a cylindrical external surface. The helicoid scanning path 17 of the tube by the ultrasound waves from an examination head such as the head 3 represented in FIG. 1 has been represented on the cylindrical external surface of the tubular cladding 16, in the case of relative displacement of the tubular cladding 16 and of the examination head in rotation and in axial translation. The path 17 may have a short pitch, for example 2 mm, in order to produce substantially continuous scanning of the tube over its entire length, in the case of a thickness examination.

As shown by FIG. 3, the wall of the tube 16 is internally bounded by successive faces 18 which are substantially of the same width and which constitute a regular prismatic surface coaxial with the axis of the tube 16.

A circular arrow 19 around the external surface of the tube 16 represents the path of a transducer of an examination head rotated about the tube 16.

A device for synchronizing the ultrasound pulses emitted by the transducer, as described with reference to FIG. 1, makes it possible to emit ultrasound pulses 20 successively around the external surface of the tube 16, so that these ultrasound pulses 20, directed radially as indicated by the arrows 21, encounter the successive faces 18a, 18b, 18c in the region of the joining edges of these faces.

The corresponding thickness signal obtained from the ultrasound pulses corresponds to constant values equal to the minimum value of the thickness of the wall of the tube.

As shown by FIG. 4, the helicoid path 17' which corresponds to the radial projection of the path 17 onto the internal surface of the tube 16 intersects the edges separating the faces 18a, 18b, 18c at the measurement points 22.

In the case of a tube having a defect, for example a number of faces different from the desired value or faces of non-constant amplitude, the thickness signal exhibits an anomaly which can be detected automatically, which is manifested by the triggering of an alarm.

As represented in FIG. 5, when each of the faces is being explored over its width, the thickness signal for each of the faces has a substantially sinusoidal shape, the thickness being a minimum in the region of the joint edges of each of the faces 18a, 18b, 18c, . . . . , 18n and a maximum for a position located at the middle of the face, equidistant from the two edges.

It is easy to examine the number of faces per revolution of the examination head, for example by counting the sinusoidal signals or their maxima.

It is also possible to examine the amplitude of each of the faces by comparing the successive sinusoidal signals.

It is also possible to examine the thickness variation of the tubular cladding over one complete revolution.

The amplitude of the faces can be measured, as has just been described, in the case of a helicoid scan during the advance of the tubular cladding inside the examination head.

The amplitude and the number of the faces are measured during one complete revolution, the duration of which is determined by the rotational measurement sensor of the head.

It is then possible to count the number of maxima or minima in the signal representing the thickness, over a period of time corresponding to the duration of one complete revolution.

This method of scanning the tube over its entire length may be expensive, because of the very large number of measurement points to be processed during the advance of the tube. However, in most cases, scanning the entire length of the tube is not necessary, studies having shown that the faces are practically constant in number and in amplitude over the entire length of a tube.

It is therefore possible to check the number of faces and measure the amplitude of the faces in a single section of a tube or over a single pitch of a helicoid path.

In all cases, the method according to the invention makes it possible to detect a defective number of faces or faces whose amplitude is not in accordance with the ideal characteristics of the multi-face tube.

The synchronization of the ultrasound pulses with respect to the scanning of the faces may be carried out by means different from a toothed ring integral with the ultrasonic examination head and a Hall probe. This device makes it possible, however, to construct a signal which depends directly on the speed of rotation of the sensor and the frequency of which is directly connected to the scanning frequency of the faces.

Any type of processing of the signals from the ultrasound transducers and of the signals produced by the synchronization or rotational examination sensors may be envisaged. Any type of supply of the transducers which is capable of being controlled in order to allow the formation of ultrasound wave trains at the desired frequency may likewise be envisaged.

Of course, the method and the device according to the invention can be used for examining multi-faced tubes other than tubular cladding of fuel rods for a nuclear reactor.

We claim:

1. Method for ultrasonic examination of faces on an internal surface of a wall of tubular cladding comprising an internal surface of substantially prismatic shape, having successive faces, said method comprising the steps of:

(a) emitting ultrasound waves in the form of pulses from outside said cladding so that said ultrasound waves directed towards an inside of said cladding pass through said wall of said cladding and scan said wall over its entire periphery;

(b) adjusting an emission frequency of said pulses as a function of a circumferential scanning speed of said cladding, so that said emission frequency is equal to an integer multiple of a scanning frequency of said faces of said cladding;

(c) recording an ultrasound signal reflected by said internal surface of said wall of said cladding; and (d) analyzing the reflected signal in order to examine said faces.

2. Method according to claim 1, comprising converting the reflected signal into a signal representing the thickness of the wall of the cladding at at least one point on each of the successive faces of the wall of the cladding.

3. Method according to claim 2, comprising adjusting the emission frequency of the ultrasound pulses to a value equal to the scanning frequency of the faces of the cladding, so as to obtain a signal representing the thickness of the cladding at a defined point on each of the successive faces and making a count of the number of faces over the entire circumference of the cladding.

4. Method according to claim 3, comprising triggering an alarm when the number of faces determined is different from a predetermined number of faces.

5. Method according to claim 2, comprising adjusting the emission frequency of the ultrasound pulses to a value corresponding to an integer multiple of the scanning frequency of the faces of the cladding, so as to obtain a signal representing the thickness of the wall of the cladding at a plurality of points on each of the faces and deducing the number of faces over the entire circumference of the cladding and the amplitude of the faces in a circumferential direction from the thickness signal.

6. Method according to claim 5, comprising emitting a signal when the number of faces or the amplitude of a face are different from predetermined values.

7. Method according to any one of claims 1 to 6, comprising scanning the wall of the cladding along a helicoid path.

8. Method according to any one of claims 1 to 6, comprising scanning the wall of the cladding along a circular path.

9. Device for ultrasonic examination of faces on an internal surface of a wall of a tube comprising an internal surface of substantially prismatic shape, having successive faces, said device comprising:

(a) an ultrasonic examination head having a tubular casing of cylindrical shape and at least one transducer oriented in order to emit ultrasound waves towards an axis of said examination head;

(b) a toothed ring fixed coaxially to said casing of said examination head on an outer lateral surface of a body of said examination head;

(c) a sensor for detecting passage of teeth of said toothed ring during rotation of said examination head about its axis; and (d) a processing and supply unit comprising an electrical means for supplying said at least one transducer of said examination head with pulses whose repetition frequency is adjusted to a value proportional to a frequency of a signal of passage of said teeth of said toothed ring of said examination head.

10. Device according to claim 9, further comprising a marking means on the outer lateral surface of the body of the examination head and a sensor for detecting the passage of the marking means during rotation of the examination head about its axis.

11. Device according to claim 9 or 10, further comprising an automatic alarm device connected to the processing unit, comprising alarm means which can be triggered automatically by means for analysis and comparison of a signal received by the transducer of the examination head.

* * * * *